Sept. 3, 1974 A. W. FISCHER Plant Pat. 3,610
AFRICAN VIOLET PLANT
Filed May 3, 1973
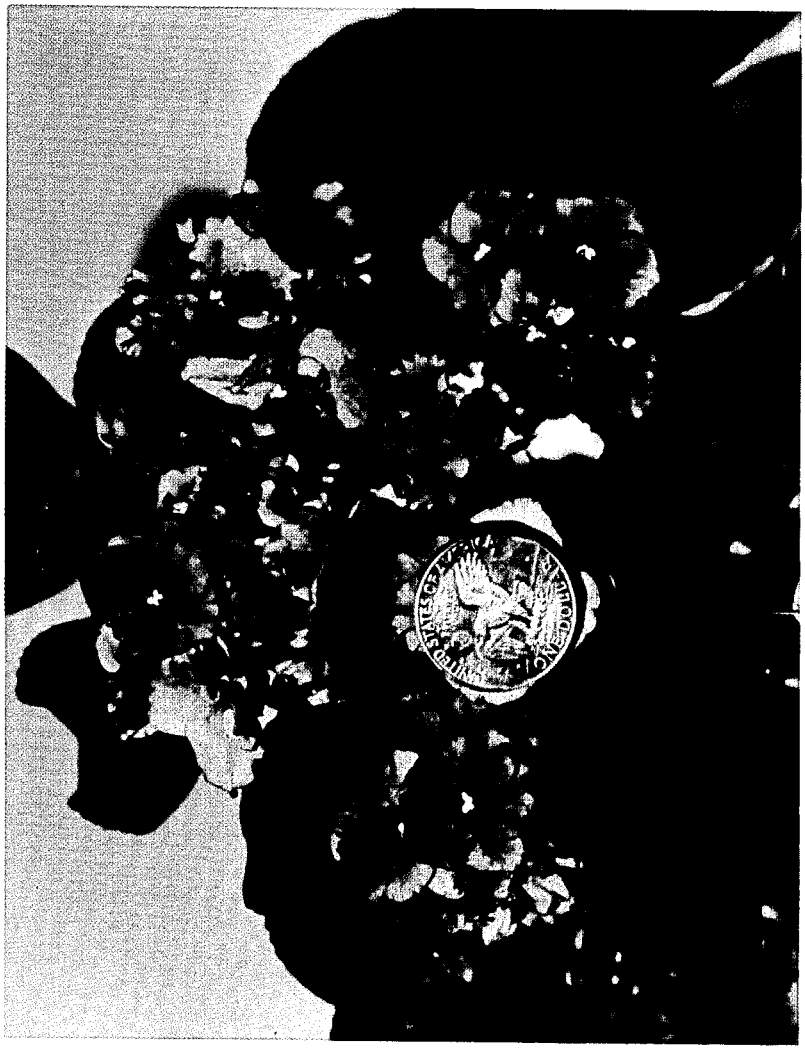

United States Patent Office

Plant Pat. 3,610
Patented Sept. 3, 1974

3,610
AFRICAN VIOLET PLANT

Arnold W. Fischer, Isernhagen, Germany, assignor to Geo. J. Ball, Inc., West Chicago, Ill.

Filed May 3, 1973, Ser. No. 356,925
Int. Cl. A01h 5/00
U.S. Cl. Plt.—69 1 Claim

ABSTRACT OF THE DISCLOSURE

A new variety of African violet plant for glass house and potted plant culture distinguished by its profuse production of large long-lasting flowers, the petals of which exhibit a variety of light to dark combinations of purple colors, the flowers appearing in clusters on sturdy, upright stems. This new plant is also characterized by its early and year around recurrent flowering habit and its condensed and abundant growth of attractive foliage.

Background of the New Plant

My herein described new African violet plant originated as a seedling of a cross made by me of two unnamed and unpatented varieties selected from among my stock of violet plants maintained by me at Isernhagen, Germany, for use in my business of breeding improved varieties of African violet plants for commercial exploitation. This plant was selected for trial because of its large and uniquely colored flowers and asexual propagation of this plant, by means of leaf cuttings, carried on by me at Isernhagen, Germany, has shown the plant to have additional commercially attractive features which appear to be fully fixed and hold true from generation to generation. This new variety of African violet is now being propagated on a commercial scale, by leaf cuttings and division of roots, at West Chicago, Ill., U.S.A., and the plants so produced retain completely the distinctive features which lead to its original adoption for commercial use.

Description of the Drawing

This new variety of African violet plant is illustrated by the accompanying full color photographic drawing which shows the color characteristics of the blossoms of the plant and their relative size, the color rendition being as nearly true as it is reasonably possible to obtain by conventional photographic procedures.

Description of the New Plant

The following is a detailed description of the new variety of African violet plant with color descriptions according to the Horticultural Colour Chart (HCC) developed and published by the British Colour Council in collaboration with The Royal Horticultural Society at London, England.

THE PLANT

Origin: Seedling.

Parentage: Seed parent—X69-22 (unnamed and unpatented). Pollen parent—X69-22. This parent plant is a variety maintained by me for breeding purposes and was inbred with selected stock to produce an improvement therein.

Classification: Botanic—Saintpaulia ionantha. Commercial—African Violet for potted plant culture.

Form: Compact potted plant (rosette arrangement).

Height: 3½ to 4 inches from base (soil) to top of flowers.

Growth: Vigorous and condensed with fairly strong petioles, which are inclined to spread horizontally, and sturdy upright peduncles.

Foliage: Quantity—abundant.

*Size of Leaf.*—About 3 inches long and 2¾ inches wide in the mature leaf.

*Shape of Leaf.*—Ovate with crenate margins.

*Texture.*—Leathery and tomentose.

*Color.*—Upper side—Ivy Green 0001060/1 edged with Spinach Green 0960/1. Under side—Magnolia Purple 03013 in center portion with Lavender Green 00761/3 edges.

THE BUD

Form: Globular—becoming urn-shaped as it opens.

Size: About ¼ inch just before opening.

Opening Rate: Very slow. 5 weeks from visible bud to opening of flower.

Color: When sepals begin to unfurl—Amethyst Violet 35/1 and Lavender Green 00761/3.

Sepals: Hooded over bud for very short period.

*Form.*—Spear shaped and upstanding. Unbranched.

*Color.*—Inside—Fern Green 0862/3. Outside—Light shade of Garnet Brown 00918/3

Calyx: Shape—synsepalous and funnel-shaped.

*Splitting.*—Calyx splits to star-shape.

*Aspect.*—Smooth on inside. Hairy on outside.

Peduncle: 2 to 2½ inches long. Erect and with tomentose aspect.

*Color.*—Light shade of Garnet Brown 00918/3.

THE FLOWER

Blooming Habit: Profuse and recurrent the year around.

Size of Flower: Large. About 1½ inches in diameter.

Shape of Flower: Very open cup-shaped when bloom first opens, becoming flat as bloom matures.

Borne: Inflorescence is a cyme.

Petalage: Number of petals—Five, three being larger than the remaining two.

*Arrangement.*—Sympetalous.

*Form.*—Orbicular with bilateral symmetry and undulated margins.

*Texture.*—Soft.

*Appearance.*—Glittery on upper surface. Satiny on bottom surface.

*Color.*—Top side of petals—Royal Purple 834 in center portion, flowing outwardly in young mature flower to Royal Purple 834/3 in top petals and Bishop Violet 34/2 in lower end of bottom petals; and in old flower flowing to Cobalt Violet 634 in top petals and Cobalt Violet 634/1 in lower petals. Reverse side of petals—Amethyst Violet 35/3 and 35/2.

Note: When this plant is exposed to high fertility in the soil the flower color can be an overall Royal Purple 834/1 in the top flower petals, and Imperial Purple 33/1 in the lower petals.

Peduncle: Main stem—About 2 to 2¼ inches long.

Pedicils—About 1 inch long.

*Strength.*—Sturdy and upright.

*Color.*—Light shade of Garnet Brown 00918/3.

Effect of Weather: Hot weather suppresses flowering and fades colors. Plant thrives in 80% to 90% humidity.

Fragrance: Slight.

Persistence: Flowers hang on and dry.

Disease Resistance: Plant exhibits a natural resistance to all common diseases as observed in environments where such diseases occur.

Lasting Quality: 14 to 18 days for the fully opened flower.

REPRODUCTIVE ORGANS

Stamens:

*Anthers.*—Two in number (each composed of two anthercells) in basifixed arrangement, about 1/16 inch in length, and Sulphur Yellow 1 in color.

*Filaments.*—1/8 inch long, Uranium Green 63 in color.

*Pollen.*—Color—White.

Pistils: One only. Length of Style—5/16 inch.

*Stigma.*—Color—Pansy Violet 033/1.

Ovaries: Thomentose and superior.

The predominate characteristics of this new variety of African violet plant reside in the unique coloring of its blooms which exhibit a variety of combinations of the herein described petal colors, which of itself is believed to be quite novel. Other advantageous characteristics are the large size of the individual flowers which develop in large clusters borne on sturdy upright stems, the vigorous and attractive foliage growth, and the early flowering and long lasting quality of the blossoms.

I claim:

1. A new variety of African violet plant, substantially as herein shown and described, characterized by its relatively large and uniquely colored blossoms which are borne in large clusters on sturdy upright stems; and by the long lasting equality of its fully opened flowers.

No references cited.

ROBERT E. BAGWILL, Primary Examiner